United States Patent
Miller et al.

(10) Patent No.: US 8,466,343 B2
(45) Date of Patent: Jun. 18, 2013

(54) ALFALFA VARIETY 07W01CZ

(75) Inventors: David J. Miller, DeForest, WI (US);
David Mickelson, DeForest, WI (US);
Gary E. Hoard, Madid, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 0 days.

(21) Appl. No.: 13/252,706

(22) Filed: Oct. 4, 2011

(65) Prior Publication Data

US 2013/0086708 A1    Apr. 4, 2013

(51) Int. Cl.
*A01H 1/00*   (2006.01)
*A01H 5/00*   (2006.01)
*A01H 5/10*   (2006.01)
*C12N 15/82*  (2006.01)

(52) U.S. Cl.
USPC ........... 800/295; 800/260; 800/278; 800/298; 435/468

(58) Field of Classification Search
None
See application file for complete search history.

(56) References Cited

U.S. PATENT DOCUMENTS 7,288,697 B2 * 10/2007 Johnson et al. ............... 800/298

* cited by examiner

*Primary Examiner* — Vinod Kumar
(74) *Attorney, Agent, or Firm* — Pioneer Hi-Bred Int'l, Inc.

(57) ABSTRACT

A novel alfalfa variety designated 07W01CZ and seed, plants and plant parts thereof. Methods for producing an alfalfa plant that comprise crossing alfalfa variety 07W01CZ with another alfalfa plant. Methods for producing an alfalfa plant containing in its genetic material one or more traits introgressed into 07W01CZ through backcross conversion and/or transformation, and to the alfalfa seed, plant and plant part produced thereby. Alfalfa seed, plant or plant part produced by crossing alfalfa variety 07W01CZ or a trait conversion of 07W01CZ with another alfalfa plant or population. Alfalfa populations derived from alfalfa variety 07W01CZ, methods for producing other alfalfa populations derived from alfalfa variety 07W01CZ and the alfalfa populations and their parts derived by the use of those methods.

14 Claims, No Drawings

US 8,466,343 B2

ALFALFA VARIETY 07W01CZ

FIELD OF INVENTION

This invention is in the field of alfalfa (*Medicago sativa*) breeding, specifically relating to an alfalfa variety designated 07W01CZ.

BACKGROUND OF THE INVENTION

Alfalfa (*Medicago sativa* L., also known as lucerne) is one of the world's most valuable forage legumes. It is grown for hay, pasture and silage, and is valued highly as a livestock feed. Alfalfa is highly effective in nitrogen fixation, and is frequently planted in crop rotation to replenish nutrients depleted from the soil by other crops such as corn.

Alfalfa originated in the Near East, in the area extending from Turkey to Iran and north into the Caucasus. From the great diversity of forms within the genus *Medicago*, two species, *M. sativa* and *M. falcata*, have become important forage plants. These species are mainly tetraploid, with 32 chromosomes, although diploid forms are known.

Alfalfa is a herbaceous perennial legume characterized by a deep tap root showing varying degrees of branching. Erect or semi-erect stems, bearing an abundance of leaves, grow to a height of 2-3 feet. The number of stems arising from a single woody crown may vary from just a few to 50 or more. New stems develop when older ones mature or have been cut or grazed. Flowers are borne on axillary racemes which vary greatly in size and number of flowers. Flower color is predominantly purple, or bluish-purple, but other colors occur. The fruit is a legume, or pod, usually spirally coiled in *M. sativa*. Seeds are small, with about 220,000/lb., and the color varies from yellow to brown. Alfalfa is widely adapted to temperature and soil conditions, except for humid tropical conditions. Reproduction in alfalfa is mainly by cross-fertilization, but substantial self-pollination may also occur. Cross-pollination is effected largely by bees.

The commercial production of seeds for growing alfalfa plants normally involves four stages, the production of breeder, foundation, certified and registered seeds. Breeder seed is the initial increase of seed of the strain which is developed by the breeder and from which foundation seed is derived. Foundation seed is the second generation of seed increase and from which certified seed is derived. Certified seeds are used in commercial crop production and are produced from foundation or certified seed. Foundation seed normally is distributed by growers or seedsmen as planting stock for the production of certified seed.

BRIEF SUMMARY OF THE INVENTION

According to the invention, there is provided a novel alfalfa variety, designated 07W01CZ and processes for making 07W01CZ. This invention relates to seed of alfalfa variety 07W01CZ, to the plants of alfalfa variety 07W01CZ, to plant parts of alfalfa variety 07W01CZ, and to processes for making an alfalfa plant that comprise crossing alfalfa variety 07W01CZ with another alfalfa plant. This invention also relates to processes for making an alfalfa plant containing in its genetic material one or more traits introgressed into 07W01CZ through backcross conversion and/or transformation, and to the alfalfa seed, plant and plant part produced by such introgression. This invention further relates to alfalfa seed, plant or plant part produced by crossing the alfalfa variety 07W01CZ or an introgressed trait conversion of 07W01CZ with another alfalfa population. This invention also relates to alfalfa populations derived from alfalfa variety 07W01CZ to processes for making other alfalfa populations derived from alfalfa variety 07W01CZ and to the alfalfa populations and their parts derived by the use of those processes.

DETAILED DESCRIPTION OF THE INVENTION AND FURTHER EMBODIMENTS

Definitions

Acid-Detergent Fiber ("ADF") approximates the amount of cellulose fiber and ash present in a feed. Forages with high ADF values are less digestible than forages with low ADF values and, therefore, provide fewer nutrients to the animal through digestion. Because of this relationship, ADF serves as an estimate of digestibility and can be used by nutritionists to predict the energy that will be available from a forage.

AOSCA. Abbreviation for Association of Official Seed Certifying Agencies.

Crude Protein ("CP") is determined by measuring the total nitrogen concentration of a forage and multiplying it by 6.25. This technique measures not only the nitrogen present in true proteins, but also that present in non-protein forms such as ammonia, urea and nitrate. Because most of the non-protein forms of nitrogen are converted to true protein by the rumen microorganisms, CP is considered by nutritionists to provide an accurate measure of the protein that will be available to ruminant animals from a given forage.

DM. Abbreviation for Dietary Dry Matter. Used to calculate yield.

Fall Dormancy ("FD")—Most alfalfa plants go dormant in the fall in preparation for winter. The onset of dormancy is triggered by a combination of day length and temperature and is genotype dependent. Fall dormancy scores measure the dormancy response of alfalfa genotypes by quantifying how early dormancy is triggered. The standard fall dormancy test requires that plants are cut off in early September with plant height measured in mid October. Early fall dormant types show very little growth after the September clipping, later fall dormant type demonstrate substantial growth. Fall dormancy is measured on a (1-11) scale, where 1=very early fall dormant and 11=non-dormant. The fall dormancy classes (2-5) are winterhardy types typically planted in the Midwest and Northeastern U.S.

In Vitro True Digestibility ("IVTD") is a measurement of digestibility utilizing actual rumen microorganisms. Although ADF serves as a good estimate of digestibility, IVID provides a more accurate assessment of a forage's feeding value by actually measuring the portion of a forage that is digested. This process is more expensive and time consuming than the analysis for ADF concentrations of a feed, but provides a more meaningful measure of forage digestibility. Techniques for measuring in vitro digestibility are based on incubating a forage sample in a solution containing rumen microorganisms for an extended period of time (usually 48 hours).

TA. Abbreviation for Tons per Acre. Used to calculate yield.

Milk Per Ton is an estimate of the milk production that could be supported by a given forage when fed as part of a total mixed ration. The equation for calculating milk per ton uses NDF and ADF to calculate total energy intake possible from the forage. After subtracting the amount of energy required for daily maintenance of the cow, the quantity of milk that could be produced from the remaining energy is calculated. The ratio of milk produced to forage consumed is then reported in the units of pounds of milk produced per ton of forage consumed. Milk per ton is useful because it characterizes forage quality in two terms that a dairy farmer is familiar with: pounds of milk and tons of forage. By combining milk per ton and dry matter yield per acre, we arrive at "milk per acre". This term is widely used to estimate the economic value of a forage.

NAAIC. Abbreviation for North America Alfalfa Improvement Conference, which is the governing body over the NA&MLVRB NA&MLVRB. Abbreviation for National Alfalfa and Miscellaneous Legume Variety Review Board. The NA&MLVRB is administered by the Association of Official Seed Certifying Agencies (AOSCA).

NAVRB. Abbreviation for National Alfalfa Variety Review Board. NAVRB recently changed its name to "National Alfalfa and Miscellaneous Legume Variety Review Board" (NA&MLVRB).

Neutral-Detergent Fiber ("NDF") represents the total amount of fiber present in the alfalfa. Because fiber is the portion of the plant most slowly digested in the rumen, it is this fraction that fills the rumen and becomes a limit to the amount of feed an animal can consume. The higher the NDF concentration of a forage, the quicker the rumen will fill and the less an animal will be able to consume. For this reason, NDF is used by nutritionists as an estimate of the quantity of forage that an animal will be able to consume. Forages with high NDF levels can limit intake to the point that an animal is unable to consume enough feed to meet their energy and protein requirements.

Percentage of alfalfa plant having resistance to potato leafhopper—Alfalfa varieties are heterogeneous populations formed by intercrossing a number of alfalfa clones. Pest resistance in alfalfa varieties is commonly measured in standard tests as the percent of plants in the population that express the resistance trait. The National Alfalfa Variety Review Board in accordance with the recommendation of the North American Alfalfa Improvement Conference has adopted a convention that uses percent resistant plants to describe levels of pest resistance. This convention is as follows: (0-5%)=susceptible, (6-15°/0)=low resistance, (16-30%)=moderate resistance, (31-50%)=resistance, and (>51%)=high resistance. With most pests, economic losses due to pest damage are minimized or eliminated with varieties containing resistance to high resistance. Individual plants can also have varying levels of resistance. The convention used for measuring PLH damage in this application was patterned after standard tests used for measuring damage/resistance to other pests. Individual plants are scored on a (1-5) scale, where 1=no damage evident and 5=severe stunting and yellowing. Plants scored as 1 and 2 are classified as resistant. The average severity index (ASI) of a variety is the average damage score for 100 random plants. The ASI is often used in combination with percent resistance to characterize pest resistance of alfalfa cultivars.

Using this standard convention, an alfalfa variety described as being resistant to PLH has between (31%-50%) of the plants in the variety being scored 1 or 2 in a standard test to measure PLH reaction. Individual alfalfa plants or clones (clonal propagules of individual genotypes) with a resistance score of 1 have very high resistance; a score of 3 show moderate resistance; and a score of 5 show no resistance.

Potato Leafhopper Resistance is a reaction of the alfalfa host plant which enables it to avoid serious damage from potato leafhopper feeding. The resistant plant reaction is to demonstrate normal growth in the presence of high populations of potato leafhoppers, whereas susceptible plants show significant stunting and yellowing in reaction to insect feeding.

Regrowth ("Rgw") Rate—Alfalfa is cut 3-4 times per year in the Midwest and Northeastern U.S. The rate of regrowth after cutting varies widely by genotype. It is generally accepted that the rate of regrowth after cutting is one of several factors that influences forage yield potential in alfalfa. Regrowth rate is measured by a visual estimation of canopy height about 10 days after cutting. The scoring system used in this patent was a (1-9 scale) with 1=slowest regrowth and 9=fastest regrowth.

Relative Feed Value ("RFV") is a numeric value assigned to forages based upon their ADF and NDF values. In this calculation, NDF is used to estimate the dry matter intake expected for a given forage, and the ADF concentration is used to estimate the digestibility of the forage. By combining these two relationships, an estimate of digestible dry matter intake is generated. This value is then reported relative to a standard forage (fall bloom alfalfa=100), and can be used to rank forages based on their anticipated feeding value. Relative feed value has been accepted in many areas as a means of estimating forage feeding value and is commonly used in determining the price of alfalfa at tested hay auctions.

Relative Forage Quality ("RFQ") is a numeric value that estimates the energy content of forage for total digestible nutrients as recommended by the National Research Council. Values are assigned to forages based upon the actual fiber digestibility (NDFd) and Total Digestible Nutrients (TDN). By combining these two relationships, an estimate of how the forage will perform in animal rations is predicted. Relative forage quality has been accepted in many areas as a means of estimating forage feeding value and is commonly used in determining the price of alfalfa at tested hay auctions or for on farm use.

Synthetic variety ("SYN") is developed by intercrossing a number of genotypes with specific favorable characteristics and/or overall general favorable qualities. Synthetic (SYN) variety can be developed by using clones, inbreds, open pollinated varieties, and/or individual heterozygous plants.

Total Digestible Nutrients ("TDN") is an estimate of the energy content of a feedstuff based on its relative proportions of fiber, fat, carbohydrate, crude protein, and ash. Because it is expensive to measure each of these components, TDN is usually estimated from ADF or IVTD. Although still used in some areas as a criteria for evaluating alfalfa hay at auctions, TDN has been shown to overestimate the energy content of low quality forages and thus does not accurately reflect the nutritional value of all forage samples.

Winterhardiness ("WH") is a measure of the ability of an alfalfa plant to survive the stresses associated with winter. Cold hardiness is a key feature of the winterhardiness trait. There is a general relationship between fall dormancy and winterhardiness, the early fall dormant types (FD2-5) being more winterhardy than the later fall dormant types (FD6-9). The winterhardiness rating used in this patent are derived from the standard test for measuring winter survival. The standard test measures plant survival and spring vigor following a winter stress enough to substantially injure check varieties.

Dormancy—Alfalfa is classified into fall dormancy groups, numbered 1 to 11, where Dormancy Group 1 is very dormant and suited for cold climates (such varieties would stop growing and go dormant over winter), and Dormancy Group 8-11 are very non-dormant and suited for very hot climates (such varieties would have high growth rates over a very long growing season and would have relatively high winter activity). Until recently, the NA&MLVRB recognized standard or check varieties for Dormancy Groups 1-11, Check cultivars are listed in the NAAIC Standard Tests to Characterize Alfalfa Cultivars, maintained online on the NAAIC's website. The check varieties for the various fall dormancy ratings/Dormancy Groups (corresponding to the rating scale used by the Certified Alfalfa Seed Council (CASC)) are as follows:

Check Cultivars

A single set of check cultivars representing fall dormancy classes (FDC) 1 to 11 are designated. These check cultivars have been selected to maintain the intended relationship between the original set of nine check cultivars (Standard Tests, March 1991, updated in 1998) and to have minimal variation across environments. The actual fall dormancy rating (FDR) based on the average University of California regression and the Certified Alfalfa Seed Council Class that each check cultivar represents are listed below.

| Variety | FDR.sup.1 | FDC.sup.2 |
|---------|-----------|-----------|
| Maverick | 0.8 | 1.0 |
| Vernal | 2.0 | 2.0 |
| 5246 | 3.4 | 3.0 |
| Legend | 3.8 | 4.0 |
| Archer | 5.3 | 5.0 |
| ABI 700 | 6.3 | 6.0 |
| Dona Ana | 6.7 | 7.0 |
| Pierce | 7.8 | 8.0 |
| CUF101 | 8.9 | 9.0 |
| UC-1887 | 9.9 | 10.0 |
| UC-1465 | 11.2 | 11.0 |

The .sup.1 number corresponds to the value calculated using the University of California regression equation.

The .sup.2 number corresponds to fall dormancy class used by the Certified Alfalfa Seed Council (CASC).

Morphological and Physiological Characteristics of Alfalfa Variety 07W01CZ

Alfalfa variety 07W01CZ is a synthetic variety with 11 parent clones. Parent clones were selected from Pioneer experimentals for forage yield, persistence and or resistance to one or more of the following pests: potato leafhopper, bacterial wilt, *Fusarium wilt, Verticillium wilt*, anthracnose (Race 1), *Phytophthora* root rot, and *Aphanomyces* root rot (Races 1 and 2). Parent clones were identified using a combination of genotypic and phenotypic selection in nursery and agronomic tests.

Alfalfa variety 07W01CZ is adapted to the North Central and East Central regions of the U.S. 07W01CZ has been tested in Illinois, Iowa, and Wisconsin, and is intended for use in the North Central, East Central, Moderately Winterhardy Intermountain, Winterhardy Intermountain, and the Great Plains regions of the U.S. and Canada.

Alfalfa variety 07W01CZ is Moderately Dormant, similar to FD5 check. Flower color (Syn2) is 94% purple, 1% cream, 4% variegated, and 1% white.

Alfalfa variety 07WO1CZ is highly resistant to anthracnose (Race 1), *Aphanomyces* root rot (Races 1 and 2), bacterial wilt, *Verticillium wilt, Fusarium wilt*, spotted alfalfa aphid, pea aphid, *Phytophthora* root rot, and potato leafhopper, and is Moderately Resistant to stem nematode. Reaction to blue alfalfa aphid and root knot nematode (*M. hapla*) has not been tested.

Use of 07W01CZ in Alfalfa Breeding

Alfalfa is an auto-tetraploid and is frequently self-incompatible in breeding. When selfed, little or no seed is produced, or the seed may not germinate, or when it does may have reduced vigor and may later stop growing. Typically, fewer than five percent of selfed crosses produce seed. When a very small population is crossbred, inbreeding depression occurs, and traits of interest, such as quality, yield, and resistance to a large number of pests (e.g., seven or eight different pests), are lost. Thus, producing a true breeding parent for hybrids is not possible, which complicates breeding substantially.

Efforts to develop alfalfa varieties having improved traits and increased production have focused on breeding for disease, insect, or nematode resistance, persistence, adaptation to specific environments, increased yield, and improved quality. Breeders have had some success in breeding for increased herbage quality and forage yield, although there are significant challenges.

Breeding programs typically emphasize maximizing heterogeneity of a given alfalfa variety to improve yield and stability. However, this generally results in wide variations in characteristics such as flowering dates, flowering frequency, development rate, growth rate, fall dormancy and winter hardiness. Prior art breeding methods do not emphasize improving the uniformity of these characteristics.

Some sources indicate that there are nine major germplasm sources of alfalfa: *M. falcata, Ladak, M. varia, Turkistan, Flemish, Chilean, Peruvian, Indian*, and *African*. Tissue culture of explant source tissue, such as mature cotyledons and hypocotyls, demonstrates the regeneration frequency of genotypes in most cultivars is only about 10 percent. Seitz-Kris, M. H. and E. T. Bingham, In vitro Cellular and Developmental Biology 24 (10):1047-1052 (1988). Efforts have been underway to improve regeneration of alfalfa plants from callus tissue. E. T. Bingham, et. al., Crop Science 15:719-721 (1975).

Another aspect of the present invention provides a method for producing first-generation synthetic variety alfalfa seed comprising crossing a first parent alfalfa plant with a second parent alfalfa plant and harvesting resultant first-generation (F1) alfalfa seed, wherein said first or second parent alfalfa plant is one of the alfalfa plants of the present invention described above.

There is a need in the art for producing alfalfa having agronomically desirable traits and breeding methods that result in a high degree of hybridity, uniformity of selected traits, and acceptable seed yields.

Male Sterility

The present invention also provides a method of obtaining alfalfa populations using cytoplasmic male sterile alfalfa populations (A populations), maintainer alfalfa populations (B populations), and male fertile pollenizer populations (C populations) as described in detail in the examples.

Male sterile A populations may be identified by evaluating pollen production using the Pollen Production Index (P.P.I.), which recognizes four distinct classes:

1. Male Sterile Plants (MS) PPI=0
   No visible pollen can be observed with the naked eye when flower is tripped with a black knife blade.
2. Partial Male Sterile Plant (PMS) PPI=0.1
   A trace of pollen is found with the naked eye when flower is tripped with a black knife blade.
3. Partial Fertile Plant (PF) PPI=0.6
   Less than a normal amount of pollen can be observed with the naked eye when flower is tripped with a black knife blade.
4. Fertile Plant (F) PPI=1.0
   Normal amounts of pollen can be observed when flower is tripped with a black knife blade.

The cells of the cytoplasmic male sterile (A population) alfalfa plants contain sterile cytoplasm and the non-restorer gene. The maintainer population (B population) is a male and female fertile plant, and when crossed with an A population plant, maintains the male sterility of the cytoplasmic male sterile plant in the progeny. The cells of a maintainer population plant contain normal cytoplasm and the non-restorer gene. Methods for identifying cytoplasmic male sterile and maintainer populations of alfalfa are well known to those versed in the art of alfalfa plant breeding (e.g., see U.S. Pat. No. 3,570,181, which is incorporated by reference herein). A pollenizer population (C population) is a fertile plant containing both male and female parts.

Briefly, the method of the invention is performed as follows:

1. Alfalfa plants with desirable agronomic traits are selected. Male sterile A population plants are selected from male sterile ("female") populations, maintainer B population plants are selected from maintainer populations, and pollenizer C population plants are selected from restorer populations, or from clonal or synthetic populations.
2. The selected A and B populations are grown from cuttings or seed and cross pollinated using bees to produce male sterile breeder and foundation seeds. Seeds are harvested from cytoplasmic male sterile plants only.
3. Selected pollenizer plants are selfed or interpollinated by bees to produce breeder and foundation pollenizer seeds and the seed is harvested in bulk.
4. For large scale commercial production, male sterile seeds and pollenizer seeds are planted at a ratio of male sterile seeds and male fertile (pollenizer) seeds of about 4:1, and the plants grown therefrom are pollinated.
5. Seeds are harvested in bulk from the plants grown from the seed of step 4, above.
6. Optionally, the percentage hybridity can be determined using either genetic or morphological markers.

Cytoplasmic male sterile populations may be maintained by vegetative cuttings. Maintainer populations can be maintained by cuttings or self-pollination. Male sterile plants can be obtained by cross-pollinating cytoplasmic male sterile plants with maintainer plants. Pollenizer populations can be maintained by selfing or, if more than two clones are used, by cross-pollination.

Preferably, at least one of the alfalfa plant populations used in developing alfalfa plants according to the method of the present invention has at least one desirable agronomic trait, which may include, for example, resistance to disease or insects, cold tolerance, increased persistence, greater forage yield or seed yield, improved forage quality, uniformity of growth rate, and uniformity of time of maturity.

In the controlled pollination step, the cytoplasmic male sterile plants are typically grown in separate rows from the maintainer plants. The plants are pollinated by pollen-carrying insects, such as bees. Segregating the male sterile and maintainer plants facilitates selective harvest of seed from the cytoplasmic male sterile plants.

The male sterile seed and male fertile seed is preferably provided as a random mixture of the seed in a ratio of about 4:1, which would provide for random distribution of the male sterile and male fertile plants grown therefrom and random pollination of the alfalfa plants. As one of skill in the art will appreciate, one could also practice the method of the invention using designed distribution of male sterile and male fertile populations within a field and subsequent pollination by pollen-carrying insects.

One of ordinary skill in the art will appreciate that any suitable male sterile population, maintainer population, and pollenizer population could be successfully employed in the practice of the method of the invention.

Tissue Culture

Yet another embodiment is a tissue culture of regenerable cells derived, in whole or in part, from an alfalfa plant of synthetic variety named 07W01CZ. In one such embodiment, the cells regenerate plants having substantially all the morphological and physiological characteristics of the synthetic alfalfa variety named 07W01CZ that are described in the attached tables. Some embodiments include such a tissue culture that includes cultured cells derived, in whole or in part, from a plant part selected from the group consisting of leaves, roots, root tips, root hairs, anthers, pistils, stamens, pollen, ovules, flowers, seeds, embryos, stems, buds, cotyledons, hypocotyls, cells and protoplasts. Another embodiment is an alfalfa plant regenerated from such a tissue culture, having all the morphological and physiological characteristics of synthetic alfalfa variety 07W01CZ.

Some methods for regeneration of alfalfa plants from tissue culture are described in U.S. Pat. No. 5,324,646 issued Jun. 28, 1994, which is hereby incorporated by reference. Additionally, researchers believe that somatic embryogenesis in alfalfa is heritable, and is controlled by relatively few genes. Efforts at improving regeneration have thus been directed towards isolation of the genetic control of embryogenesis, and breeding programs which would incorporate such information. See, e.g., M. M. Hernandez-Fernandez, and B. R. Christie, Genome 32:318-321 (1989); I. M. Ray and E. T. Bingham, Crop Science 29:1545-1548 (1989).

As used herein, the term "plant" includes plant cells, plant protoplasts, plant cells of tissue culture from which alfalfa plants can be regenerated, plant calli, plant clumps, and plant cells that are intact in plants or parts of plants such as pollen, flowers, seeds, leaves, stems, and the like.

Tissue culture of alfalfa is further described in Saunders, J. W. and Bingham, E. T., (1971) Production of alfalfa plants from callus tissue, Crop Sci 12; 804-808, and incorporated herein by reference.

Transformation

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are inserted into the genome using transformation are referred to herein collectively as "transgenes". In some embodiments of the invention, a transformed variant of 07W01CZ may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present invention also relates to transformed versions of the claimed alfalfa variety 07W01CZ as well as hybrid combinations thereof.

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88 and Armstrong, "The First Decade of Maize Transformation: A Review and Future Perspective" (Maydica 44:101-109, 1999). Specific to alfalfa, see "Efficient *Agrobacterium*-mediated transformation of alfalfa using secondary somatic embryogenic callus", Journal of the Korean Society of Grassland Science 20 (1): 13-18 2000, E. Charles Brummer, "Applying Genomics to Alfalfa Breeding Programs" Crop Sci. 44:1904-1907 (2004), and "Genetic transformation of commercial breeding populations of alfalfa (*Medicago sativa*)" Plant Cell Tissue and Organ Culture 42 (2): 129-140 1995 which are incorporated by reference for this purpose. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into the genome of a particular alfalfa plant using transformation techniques, could be moved into the genome of another population using traditional breeding techniques that are well known in the plant breeding arts. For example, a backcrossing approach may be used to move a transgene from a transformed alfalfa plant to an elite population, and the resulting progeny would then comprise the transgene(s).

Various genetic elements can be introduced into the plant genome using transformation. These elements include, but are not limited to genes; coding sequences; inducible, constitutive, and tissue specific promoters; enhancing sequences; and signal and targeting sequences. For example, see the traits, genes and transformation methods listed in U.S. Pat. No. 6,118,055.

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92-6 (1981).

A genetic map can be generated, primarily via conventional Restriction Fragment Length Polymorphisms (RFLP), Polymerase Chain Reaction (PCR) analysis, Simple Sequence Repeats (SSR) and Single Nucleotide Polymorphisms (SNP) that identifies the approximate chromosomal location of the integrated DNA molecule. For exemplary methodologies in this regard, see Glick and Thompson, Methods in Plant Molecular Biology and Biotechnology 269-284 (CRC Press, Boca Raton, 1993). Specific to alfalfa, see Construction of an improved linkage map of diploid alfalfa (*Medicago sativa*), Theoretical and Applied Genetics 100 (5): 641-657 March, 2000 and Isolation of a full-length mitotic cyclin cDNA clone CyclIIMs from *Medicago sativa*: Chromosomal mapping and expression, Plant Molecular Biology 27 (6): 1059-1070 1995 which are incorporated by reference for this purpose.

Wang et al. discuss "Large Scale Identification, Mapping and Genotyping of Single-Nucleotide Polymorphisms in the Human Genome", Science, 280:1077-1082, 1998, and similar capabilities are becoming increasingly available for many plant genomes. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques. SNPs may also be used alone or in combination with other techniques.

Likewise, by means of the present invention, plants can be genetically engineered to express various phenotypes of agronomic interest. Through the transformation of alfalfa the expression of genes can be altered to enhance disease resistance, insect resistance, herbicide resistance, agronomic, grain quality and other traits. Transformation can also be used to insert DNA sequences which control or help control male-sterility. DNA sequences native to alfalfa as well as non-native DNA sequences can be transformed into alfalfa and used to alter levels of native or non-native proteins. Various promoters, targeting sequences, enhancing sequences, and other DNA sequences can be inserted into the alfalfa genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, *The Maize Handbook* ch. 118 (Springer-Verlag 1994) or other genetic elements such as a FRT, Lox or other site specific integration site, antisense technology (see, e.g., Sheehy et al. (1988) *PNAS* USA 85:8805-8809; and U.S. Pat. Nos. 5,107,065; 5,453,566; and 5,759,829); co-suppression (e.g., Taylor (1997) *Plant Cell* 9:1245; Jorgensen (1990) *Trends Biotech.* 8(12):340-344; Flavell (1994) *PNAS* USA 91:3490-3496; Finnegan et al. (1994) *Bio/Technology* 12: 883-888; and Neuhuber et al. (1994) *Mol. Gen. Genet.* 244: 230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *PNAS USA* 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); MicroRNA (Aukerman & Sakai (2003) *Plant Cell* 15:2730-2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Exemplary nucleotide sequences that may be altered by genetic engineering include, but are not limited to, those categorized below.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains.

See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*); McDowell & Woffenden, (2003) Trends Biotechnol. 21(4): 178-83 and Toyoda et al., (2002) Transgenic Res. 11(6):567-82. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; WO 91/14778; WO 99/31248; WO 01/12731; WO 99/24581; WO 97/40162 and U.S. application Ser. Nos. 10/032,717; 10/414,637; and 10/606,320.

(C) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(D) An insect-specific peptide which, upon expression, disrupts the physiology of the affected pest. For example, see the disclosures of Regan, J. Biol. Chem. 269: 9 (1994) (expression cloning yields DNA coding for insect diuretic hormone receptor); Pratt et al., Biochem. Biophys. Res. Comm. 163: 1243 (1989) (an allostatin is identified in *Diploptera puntata*); Chattopadhyay et al. (2004) Critical Reviews in Microbiology 30 (1): 33-54 2004; Zjawiony (2004) J Nat Prod 67 (2): 300-310; Carlini & Grossi-de-Sa (2002) Toxicon, 40 (11): 1515-1539; Ussuf et al. (2001) Curr Sci. 80 (7): 847-853; and Vasconcelos & Oliveira (2004) Toxicon 44 (4): 385-403. See also U.S. Pat. No. 5,266,317 to Tomalski et al., who disclose genes encoding insect-specific toxins.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23: 691 (1993), who teach the nucleotide sequence of a cDNA encoding tobacco hookworm chitinase, and Kawalleck et al., Plant Molec. Biol. 21: 673 (1993), who provide the nucleotide sequence of the parsley ubi4-2 polyubiquitin gene, U.S. application Ser. Nos. 10/389,432, 10/692,367, and U.S. Pat. No. 6,563,020.

(G) A molecule that stimulates signal transduction. For example, see the disclosure by Botella et al., Plant Molec. Biol. 24: 757 (1994), of nucleotide sequences for mung bean calmodulin cDNA clones, and Griess et al., Plant Physiol. 104: 1467 (1994), who provide the nucleotide sequence of a maize calmodulin cDNA clone.

(H) A hydrophobic moment peptide. See PCT application WO 95/16776 and U.S. Pat. No. 5,580,852 (disclosure of peptide derivatives of Tachyplesin which inhibit fungal plant pathogens) and PCT application WO 95/18855 and U.S. Pat. No. 5,607,914) (teaches synthetic antimicrobial peptides that confer disease resistance).

(I) A membrane permease, a channel former or a channel blocker. For example, see the disclosure by Jaynes et al., Plant Sci. 89: 43 (1993), of heterologous expression of a cecropin-beta lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A virus-specific antibody. See, for example, Tavladoraki et al., Nature 366: 469 (1993), who show that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., Bio/Technology 10: 1436 (1992). The cloning and characterization of a gene which encodes a bean endopolygalacturonase-inhibiting protein is described by Toubart et al., Plant J. 2: 367 (1992).

(N) A developmental-arrestive protein produced in nature by a plant. For example, Logemann et al., Bio/Technology 10: 305 (1992), have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, S., Current Biology, 5(2):128-131 (1995), Pieterse & Van Loon (2004) Curr. Opin. Plant Bio. 7(4):456-64 and Somssich (2003) Cell 113(7):815-6.

(P) Antifungal genes (Cornelissen and Melchers, Pl. Physiol. 101:709-712, (1993) and Parijs et al., Planta 183: 258-264, (1991) and Bushnell et al., Can. J. of Plant Path. 20(2):137-149 (1998). Also see U.S. application Ser. No. 09/950,933.

(Q) Detoxification genes, such as for fumonisin, beauvericin, moniliformin and zearalenone and their structurally related derivatives. For example, see U.S. Pat. No. 5,792,931.

(R) Cystatin and cysteine proteinase inhibitors. See U.S. application Ser. No. 10/947,979.

(S) Defensin genes. See WO03000863 and U.S. application Ser. No. 10/178,213.

(T) Genes conferring resistance to nematodes. See WO 03/033651 and Urwin et. al., Planta 204:472-479 (1998), Williamson (1999) Curr Opin Plant Bio. 2(4):327-31.

2. Transgenes that Confer Resistance to a Herbicide, for Example:

(A) A herbicide that inhibits the growing point or meristem, such as an imidazolinone or a sulfonylurea. Exemplary genes in this category code for mutant ALS and AHAS enzyme as described, for example, by Lee et al., *EMBO J.* 7: 1241 (1988), and Miki et al., *Theor. Appl. Genet.* 80: 449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference for this purpose.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. application Ser. Nos. 01/46227; 10/427,692 and 10/427,692. A DNA molecule encoding a mutant aroA gene can be obtained under ATCC accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European Patent No. 0 242 246 and 0 242 236 to Leemans et al. De Greef et al., *Bio/Technology* 7: 61 (1989), describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference for this purpose. Exemplary genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs+ genes) and a benzonitrile (nitrilase gene). Przibilla et al., *Plant Cell* 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

(D) Acetohydroxy acid synthase, which has been found to make plants that express this enzyme resistant to multiple types of herbicides, has been introduced into a variety of plants (see, e.g., Hattori et al. (1995) Mol Gen Genet. 246: 419). Other genes that confer resistance to herbicides include: a gene encoding a chimeric protein of rat cytochrome P4507A1 and yeast NADPH-cytochrome P450 oxidoreductase (Shiota et al. (1994) Plant Physiol. 106:17), genes for glutathione reductase and superoxide dismutase (Aono et al. (1995) Plant Cell Physiol 36:1687, and genes for various phosphotransferases (Datta et al. (1992) Plant Mol Biol 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825.

3. Transgenes that Confer or Contribute to an Altered Grain Characteristic, Such as:

(A) Altered fatty acids, for example, by
(1) Down-regulation of stearoyl-ACP desaturase to increase stearic acid content of the plant. See Knultzon et al., *Proc. Natl. Acad. Sci. USA* 89: 2624 (1992) and WO99/64579 (Genes for Desaturases to Alter Lipid Profiles in Corn),
(2) Elevating oleic acid via FAD-2 gene modification and/or decreasing linolenic acid via FAD-3 gene modification (see U.S. Pat. Nos. 6,063,947; 6,323,392; 6,372,965 and WO 93/11245),
(3) Altering conjugated linolenic or linoleic acid content, such as in WO 01/12800,
(4) Altering LEC1, AGP, Dek1, Supera1, mi1ps, various Ipa genes such as Ipa1, Ipa3, hpt or hggt. For example, see WO 02/42424, WO 98/22604, WO 03/011015, U.S. Pat. No. 6,423,886, U.S. Pat. No. 6,197,561, U.S. Pat. No. 6,825,397, US2003/0079247, US2003/0204870, WO02/057439, WO03/011015 and Rivera-Madrid, R. et. al. Proc. Natl. Acad. Sci. 92:5620-5624 (1995).

(B) Altered phosphorus content, for example, by the
(1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.
(2) Up-regulation of a gene that reduces phytate content. In alfalfa, this, for example, could be accomplished, by cloning and then re-introducing DNA associated with one or more of the alleles, such as the LPA alleles, identified in maize mutants characterized by low levels of phytic acid, such as in Raboy et al., *Maydica* 35: 383 (1990) and/or by altering inositol kinase activity as in WO 02/059324, US2003/0009011, WO 03/027243, US2003/0079247, WO 99/05298, U.S. Pat. No. 6,197,561, U.S. Pat. No. 6,291,224, U.S. Pat. No. 6,391,348, WO2002/059324, US2003/0079247, Wo98/45448, WO99/55882, WO01/04147.

(C) Altered carbohydrates effected, for example, by altering a gene for an enzyme that affects the branching pattern of starch or a gene altering thioredoxin (See U.S. Pat. No. 6,531,648). See Shiroza et al., J. Bacteriol. 170: 810 (1988) (nucleotide sequence of *Streptococcus mutans* fructosyltransferase gene), Steinmetz et al., Mol. Gen. Genet. 200: 220 (1985) (nucleotide sequence of *Bacillus subtilis* levansucrase gene), Pen et al., Bio/Technology 10: 292 (1992) (production of transgenic plants that express *Bacillus licheniformis* alpha-amylase), Elliot et al., Plant Molec. Biol. 21: 515 (1993) (nucleotide sequences of tomato invertase genes), Søgaard et al., J. Biol. Chem. 268: 22480 (1993) (site-directed mutagenesis of barley alpha-amylase gene), and Fisher et al., Plant Physiol. 102: 1045 (1993) (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US2003/0163838, US2003/0150014, US2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US2004/0025203 (UDPGdH), U.S. Pat. No. 6,194,638 (RGP).

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N—Ac—PPT (WO 01/29237).

(B) Introduction of various stamen-specific promoters (WO 92/13956, WO 92/13957).

(C) Introduction of the barnase and the barstar gene (Paul et al. Plant Mol. Biol. 19:611-622, 1992).

For additional examples of nuclear male and female sterility systems and genes, see also, U.S. Pat. No. 5,859,341; U.S. Pat. No. 6,297,426; U.S. Pat. No. 5,478,369; U.S. Pat. No. 5,824,524; U.S. Pat. No. 5,850,014; and U.S. Pat. No. 6,265,640; all of which are hereby incorporated by reference.

5. Genes that create a site for site specific DNA integration. This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925-932 and WO 99/25821, which are hereby incorporated by reference. Other systems that may be used include the Gin recombinase of phage Mu (Maeser et al., 1991; Vicki Chandler, *The Maize Handbook* ch. 118 (Springer-Verlag 1994), the Pin recombinase of *E. coli* (Enomoto et al., 1983), and the R/RS system of the pSR1 plasmid (Araki et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. No. 5,892,009, U.S. Pat. No. 5,965,705, U.S. Pat. No. 5,929,305, U.S. Pat. No. 5,891,859, U.S. Pat. No. 6,417,428, U.S. Pat. No. 6,664,446, U.S. Pat. No. 6,706,866, U.S. Pat. No. 6,717,034, U.S. Pat. No. 6,801,104, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521, and WO9938977 describing genes, including CBF genes and transcription factors effective in mitigating the negative effects of freezing, high salinity, and drought on plants, as well as conferring other positive effects on plant phenotype; US2004/0148654 and WO01/36596 where abscisic acid is altered in plants resulting in improved plant phenotype such as increased yield and/or increased tolerance to abiotic stress; WO2000/006341, WO04/090143, U.S. application Ser. Nos. 10/817,483 and 09/545,334 where cytokinin expression is modified resulting in plants with increased stress tolerance, such as drought tolerance, and/or increased yield. Also see WO0202776, WO2003052063, JP2002281975, U.S. Pat. No. 6,084,153, WO0164898, U.S. Pat. No. 6,177,275, and U.S. Pat. No. 6,107,547 (enhancement of nitrogen utilization and altered nitrogen responsiveness). For ethylene alteration, see US20040128719, US20030166197 and WO200032761. For plant transcription factors or transcriptional regulators of abiotic stress, see e.g. US20040098764 or US20040078852.

Other genes and transcription factors that affect plant growth and agronomic traits such as yield, flowering, plant growth and/or plant structure, can be introduced or introgressed into plants, see e.g. WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. No. 6,794,560, U.S. Pat. No. 6,307,126 (GAI), WO99/09174 (D8 and Rht), and WO2004076638 and WO2004031349 (transcription factors).

TABLE 1

Yield data for 07W01CZ in DM in T/A compared to other varieties at multiple locations.

| Test Location | Date Planted Mo/Yr | Syn Gen | Year Harvested | No. Cuts | 07W01CZ | 53H92 | GAR6426 | WLRWL 345LH | LSD .05 | CV % |
|---|---|---|---|---|---|---|---|---|---|---|
| Plateville, WI | 05/07 | 1 | 2008 | 4 | 6.49 | 5.82 | 6.2 | 6.97 | 0.5 | 4.7 |
| | 05/07 | 1 | 2009 | 4 | 4.75 | 4.06 | 4.45 | 4.74 | 0.41 | 5.8 |
| Arlington, WI | 05/07 | 1 | 2008 | 4 | 6.3 | 6.28 | 6.58 | 6.87 | 0.37 | 3.8 |
| | 05/07 | 1 | 2009 | 4 | 5.57 | 5.16 | 5.45 | 5.41 | 0.3 | 3.5 |
| Princeton, IL | 05/07 | 1 | 2008 | 4 | 5.69 | 5.3 | 5.54 | 5.6 | 0.36 | 4.1 |
| | 05/07 | 1 | 2009 | 4 | 4.77 | 4.44 | 4.27 | 4.66 | 0.43 | 6.1 |
| Johnston, IA | 05/07 | 1 | 2008 | 4 | 5.09 | 4.98 | 4.53 | 4.82 | 0.44 | 5.7 |

TABLE 2

Persistence data for 07W01CZ compared to other varieties at multiple locations (Percent of stand).

| Test Location | Syn Gen | Date Seeded (Mo/Yr) | No. of Years Harvested | No. of Harvests | Date of Readings Initial (Mo/Yr) | Date of Readings Final (Mo/Yr) | 07W01CZ Initial | 07W01CZ Final | 55V48 Initial | 55V48 Final | FG4P424 Initial | FG4P424 Final | LSD .05 | CV % |
|---|---|---|---|---|---|---|---|---|---|---|---|---|---|---|
| Princeton, IL | 1 | 05/07 | 3 | 12 | 08/09 | | 100 | 97 | 100 | 98 | 100 | 97.4 | 4 | 2.5 |

TABLE 3

Anthracnose (Race 1) Disease Scores for 07W01CZ.

Test conducted by Pioneer Hi-Bred International Inc., at Arlington, WI. Kind of test conducted is Greenhouse.

| | Variety | Resistance Class | Year Tested | Syn Gen | Unadjusted % R | Adjusted % R | Score |
|---|---|---|---|---|---|---|---|
| | 07W01CZ | HR | 2007 | 1 | 88.9 | 95.8 | |
| 1. | Arc | HR | | | 65.0 | 70.0 | |
| 2. | Saranac AR | R | | | | | |
| 3. | Saranac | S | | | 0.7 | 0.8 | |
| 4. | | | | | | | |
| | Test Mean: | | | | 57.3 | 61.6 | |
| | L.S.D. (.05%) | | | | 9.6 | 10.3 | |
| | C.V. (%) | | | | 12.1 | | |

TABLE 4

Bacterial Wilt Disease Scores for 07W01CZ.

Test conducted by Pioneer Hi-Bred International Inc., at Arlington, WI. Kind of test conducted is Greenhouse.

|    | Variety | Resistance Class | Year Tested | Syn Gen | Unadjusted % R | Adjusted % R | Score |
|----|---------|------------------|-------------|---------|----------------|--------------|-------|
|    | 07W01CZ | HR | 2010/2011 | 2 | 69.0 | 67.7 | |
| 1. | Vernal | R | | | 43.4 | 42.0 | |
| 2. | Narragansett | S | | | | | |
| 3. | Sonora | S | | | 2.7 | 2.6 | |
| 4. | | | | | | | |
|    | Test Mean: | | | | 61.5 | 59.5 | |
|    | L.S.D. (.05%) | | | | 10.3 | 9.9 | |
|    | C.V. (%) | | | | 11.8 | 11.8 | |

TABLE 5

Fusarium Wilt Disease Scores for 07W01CZ.

Test conducted by Pioneer Hi-Bred International Inc., at Arlington, WI. Kind of test conducted is Greenhouse.

|    | Variety | Resistance Class | Year Tested | Syn Gen | Unadjusted % R | Adjusted % R | Score |
|----|---------|------------------|-------------|---------|----------------|--------------|-------|
|    | 07W01CZ | HR | 2009 | 1 | 62.4 | 63.9 | |
| 1. | Agate (Field) | HR | | | 52.8 | 54.0 | |
|    | Agate (Greenhouse) | R | | | | | |
| 2. | Moapa 69 (Field) | HR | | | | | |
|    | Moapa 69 (Greenhouse) | HR | | | | | |
| 3. | Narragansett (Field) | MR | | | | | |
|    | Narragansett (Greenhouse) | N/A | | | | | |
| 4. | MNGN-1 | S | | | 2.6 | 2.7 | |
|    | Test Mean: | | | | 49.6 | 50.8 | |
|    | L.S.D. (.05%) | | | | 13.9 | 14.2 | |
|    | C.V. (%) | | | | 16.4 | | |

TABLE 6

Verticillium Wilt Disease Scores for 07W01CZ.

Test conducted by Pioneer Hi-Bred International Inc., at Connell, WA. Kind of test conducted is Greenhouse.

|    | Variety | Resistance Class | Year Tested | Syn Gen | Unadjusted % R | Adjusted % R | Score |
|----|---------|------------------|-------------|---------|----------------|--------------|-------|
|    | 07W01CZ | HR | 2010 | 1 | 59.4 | 66.2 | |
| 1. | Vertus | R | | | | | |
| 2. | Oneida VR | HR | | | 53.8 | 60.0 | |
| 3. | Saranac | S | | | 3.2 | 3.6 | |
| 4. | | | | | | | |
|    | Test Mean: | | | | 45.6 | 50.9 | |
|    | L.S.D. (.05%) | | | | 12.00 | 13.3 | |
|    | C.V. (%) | | | | 23.2 | | |

TABLE 7

Phytophthora Root Rot Disease Scores for 07W01CZ.

Test conducted by Pioneer Hi-Bred International Inc., at Arlington, WI. Kind of test conducted is Greenhouse.

| | Variety | Resistance Class | Year Tested | Syn Gen | Unadjusted % R | Adjusted % R | Score |
|---|---|---|---|---|---|---|---|
| | 07W01CZ | HR | 2007 | 1 | 78.7 | 85.1 | |
| 1. | WAPH-1 (seedling) | HR | | | 50.9 | 55.0 | |
| 2. | MNP-D1 (seedling) | R | | | | | |
| 3. | Agate | R | | | | | |
| 4. | Saranac | S | | | 0 | 0 | |
| | Test Mean: | | | | 65.8 | 71.2 | |
| | L.S.D. (.05%) | | | | 14.8 | 16 | |
| | C.V. (%) | | | | 16.3 | | |

TABLE 8

Aphanomyces Root Rot (Race 1) Disease Scores for 07W01CZ.

Test conducted by Pioneer Hi-Bred International Inc. at Arlington, WI. Kind of test conducted is Greenhouse.

| | Variety | Resistance Class | Year Tested | Syn Gen | Unadjusted % R | Adjusted % R | Score |
|---|---|---|---|---|---|---|---|
| | 07W01CZ | HR | 2007 | 1 | 58.0 | 75.0 | |
| 1. | WAPH-1 (Race 1) | R | | | 38.7 | 50.0 | |
| 2. | WAPH-1 (Race 2) | S | | | | | |
| 3. | WAPH-5 (Race 2) | R | | | | | |
| 4. | Saranac (Races 1 & 2) | S | | | 2.5 | 3.2 | |
| | Test Mean: | | | | 59.5 | 76.9 | |
| | L.S.D. (.05%) | | | | 16.2 | 20.9 | |
| | C.V. (%) | | | | 19.6 | | |

TABLE 9

Pea Aphid Insect Scores for Scores for 07W01CZ.

Test conducted by Pioneer Hi-Bred International Inc., at Arlington, WI. Kind of test conducted is Greenhouse.

| | Variety | Resistance Class | Year Tested | Syn Gen | Unadjusted % R | Adjusted % R | Score |
|---|---|---|---|---|---|---|---|
| | 07W01CZ | R | 2010 | 1 | 40.5 | 47.3 | |
| 1. | CUF-101 | HR | | | | | |
| 2. | PA-1 | HR | | | | | |
| 3. | Kanza | R | | | | | |
| 4. | Baker | R | | | 38.5 | 45 | |
| 5. | Caliverde | S | | | | | |
| 6. | Moapa 69 | S | | | | | |
| 7. | Vernal | S | | | | | |
| 8. | Ranger | S | | | 5.9 | 6.9 | |
| | Test Mean: | | | | 34.8 | 40.7 | |
| | L.S.D. (.05%) | | | | 8.90 | 10.4 | |
| | C.V. (%) | | | | 22.5 | | |

TABLE 10

Spotted Alfalfa Aphid Insect Scores for 07W01CZ.

Test conducted by Pioneer Hi-Bred International Inc., at Connell, WA. Kind of test conducted is Greenhouse.

| | Variety | Resistance Class | Year Tested | Syn Gen | Unadjusted % R | Adjusted % R | Score |
|---|---|---|---|---|---|---|---|
| | 07W01CZ | HR | 2010 | 1 | 48.6 | 55.7 | |
| 1. | CUF-101 | HR | | | | | |
| 2. | Baker | R | | | 43.7 | 50.0 | |
| 3. | Mesa Sirsa | R | | | | | |
| 4. | Kanza | R | | | | | |
| 5. | Caliverde | S | | | | | |
| 6. | Arc | S | | | | | |
| 7. | OK08 | S | | | | | |
| 8. | Ranger | S | | | 2.4 | 2.8 | |
| | Test Mean: | | | | 38.9 | 44.6 | |
| | L.S.D. (.05%) | | | | 12.8 | 14.6 | |
| | C.V. (%) | | | | 23.7 | | |

TABLE 11

Stem Nematode Scores for 07W01CZ.

Test conducted by Pioneer Hi-Bred International Inc., at Connell, WA. Kind of test conducted is Controlled Environment, Greenhouse.

| | Variety | Resistance Class | Year Tested | Syn Gen | Unadjusted % R | Adjusted % R | Score |
|---|---|---|---|---|---|---|---|
| | 07W01CZ | MR | 2008 | 1 | 29.8 | 29.4 | |
| 1. | Vernema | HR | | | | | |
| 2. | Lahontan | R | | | 40.5 | 40.0 | |
| 3. | Lew | R | | | | | |
| 4. | Ranger | S | | | | | |
| 5. | Moapa 69 | S | | | 2.3 | 2.3 | |
| | Test Mean: | | | | 33.3 | 32.9 | |
| | L.S.D. (.05%) | | | | 12.2 | 12.1 | |
| | C.V. (%) | | | | 26.5 | | |

TABLE 12

Aphanomyces (Race 2) Disease Scores for 07W01CZ.

Test conducted by Pioneer Hi-Bred International Inc..

| | Variety | Resistance Class | Year Tested | Syn Gen | Unadjusted % R | Adjusted % R | Score |
|---|---|---|---|---|---|---|---|
| | 07W01CZ | HR | 2007 | 1 | 54.5 | 57.1 | |
| 1. | WAPH-1 (Race 1) | R | | | | | |
| 2. | WAPH-1 (Race 2) | S | | | | | |
| 3. | WAPH-5 (Race 2) | R | | | 47.7 | 50.0 | |
| 4. | Saranac (Races 1&2) | S | | | 0.8 | 0.8 | |
| 5. | | | | | | | |
| 6. | | | | | | | |
| 7. | | | | | | | |
| 8. | | | | | | | |
| | Test Mean: | | | | 38.6 | 40.5 | |
| | L.S.D. (.05%) | | | | 18.7 | 19.6 | |
| | C.V. (%) | | | | 34.9 | | |

All disease tests conducted for National Alfalfa and Miscellaneous Legume Variety Review Board for AOSCA certification and were conducted by standard procedures and scoring systems as described in the NAAIC Standard Tests to Characterize Alfalfa Cultivars, maintained online on the NAAIC's website.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

DEPOSITS

Applicant(s) have made a deposit of at least 2500 seeds of Alfalfa Variety 07W01CZ with the American Type Culture Collection (ATCC), 10801 University Boulevard, Manassas, Va. 20110 USA, ATCC Deposit No. PTA-120133. The seeds deposited with the ATCC on Jan. 15, 2013 were taken from the deposit maintained by Pioneer Hi-Bred International, Inc., 7250 NW 62$^{nd}$ Avenue, Johnston, Iowa 50131 since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant(s) will make the deposit available to the public pursuant to 37 C.F.R. 1.808. This deposit of Alfalfa Variety 07W01CZ will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant(s) have or will satisfy all of the requirements of 37 C.F.R. §§1.801-1.809, including providing an indication of the viability of the sample upon deposit. Applicant(s) have no authority to waive any restrictions imposed by law on the transfer of biological material or its transportation in commerce. Applicant(s) do not waive any infringement of rights granted under this patent or under the Plant Variety Protection Act (7 USC 2321 et seq.). U.S. Plant Variety Protection of Alfalfa Variety 07W01CZ may be applied for. Unauthorized seed multiplication prohibited.

We claim:

1. Seed of an Alfalfa Variety 07W01CZ, representative seed having been deposited under ATCC Accession Number PTA-120133.

2. An alfalfa plant, or a part thereof, produced by growing the seed of claim 1.

3. Pollen of the plant of claim 2.

4. An ovule from the plant of claim 2.

5. A tissue culture of regenerable cells or regenerable protoplasts from the plant of claim 2.

6. A tissue culture according to claim 5, wherein a cell or protoplast of the tissue culture is derived from a tissue or cell selected from the group consisting of leaves, roots, root tips, root hairs, anthers, pistils, stamens, pollen, ovules, flowers, seeds, embryos, stems, buds, cotyledons, hypocotyls, cells and protoplasts.

7. An alfalfa plant regenerated from the tissue culture of claim 5, wherein the regenerated plant has all of the morphological and physiological characteristics of alfalfa variety 07W01CZ, representative seed of said alfalfa variety having been deposited under ATCC Accession Number PTA-120133.

8. A process for producing a first generation progeny alfalfa seed comprising crossing a first parent alfalfa plant with a second parent alfalfa plant and harvesting the resultant alfalfa seed, wherein said first parent alfalfa plant or said second parent alfalfa plant is the alfalfa plant of claim 2.

9. A process for producing an alfalfa plant or a part thereof comprising growing the seed of claim 1.

10. The seed of claim 1 further comprising a transgene.

11. The seed of claim 10 wherein the transgene confers a trait selected from the group consisting of herbicide resistance, insect resistance, disease resistance, improved digestibility, improved energy content, male sterility, and improved winterhardiness.

12. A process for producing a synthetic alfalfa plant variety, comprising crossing an alfalfa plant obtained from the seed of claim 1 with one or more other alfalfa plants.

13. A process for producing alfalfa seed comprising growing the plant of claim 2, allowing said grown plant to cross pollinate with one or more different alfalfa plants and obtain alfalfa seed from the cross pollinated plant.

14. A process for producing an alfalfa seed comprising harvesting seed of the plant or plant part of claim 2.

* * * * *